United States Patent
Chiou

(10) Patent No.: US 9,549,894 B2
(45) Date of Patent: *Jan. 24, 2017

(54) WATER-RELEASING COSMETIC COMPOSITION INCLUDING A HYDROPHOBIC SILICA

(71) Applicant: L'OREAL, Paris (FR)

(72) Inventor: Catherine Chiou, Saddle Brook, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/716,270

(22) Filed: May 19, 2015

(65) Prior Publication Data

US 2015/0250706 A1    Sep. 10, 2015

Related U.S. Application Data

(63) Continuation-in-part of application No. 13/529,113, filed on Jun. 21, 2012, now abandoned.

(51) Int. Cl.
| | |
|---|---|
| *A61K 8/894* | (2006.01) |
| *A61K 8/06* | (2006.01) |
| *A61K 8/25* | (2006.01) |
| *A61Q 19/00* | (2006.01) |
| *A61K 8/34* | (2006.01) |
| *A61K 8/891* | (2006.01) |
| *A61K 8/892* | (2006.01) |

(52) U.S. Cl.
CPC .............. *A61K 8/894* (2013.01); *A61K 8/062* (2013.01); *A61K 8/064* (2013.01); *A61K 8/25* (2013.01); *A61K 8/345* (2013.01); *A61K 8/891* (2013.01); *A61K 8/892* (2013.01); *A61Q 19/00* (2013.01); *A61K 2800/412* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 6,524,598 B2 | 2/2003 | Sunkel et al. | |
| 6,696,049 B2 | 2/2004 | Vatter et al. | |
| 2002/0119110 A1* | 8/2002 | Mahe et al. | 424/70.1 |
| 2003/0064046 A1 | 4/2003 | Omura et al. | |
| 2004/0071651 A1 | 4/2004 | Deckner et al. | |
| 2006/0292192 A1* | 12/2006 | Hasenzahl et al. | 424/401 |
| 2007/0264210 A1* | 11/2007 | Robinson | 424/59 |
| 2009/0035236 A1* | 2/2009 | Maes | A61K 8/06 424/59 |
| 2010/0310617 A1 | 12/2010 | Zhang et al. | |
| 2011/0256077 A1 | 10/2011 | Hayakawa | |
| 2013/0345315 A1 | 12/2013 | Chiou | |
| 2013/0345317 A1 | 12/2013 | Chiou | |
| 2014/0308323 A1* | 10/2014 | Midha et al. | 424/401 |

OTHER PUBLICATIONS

Dow Corning, Silicone Surfactants, http://www.dowcorning.com/content/discover/discoverchem/forms-mixtures-surfactants.aspx, retrieved online on May 18, 2015.

\* cited by examiner

*Primary Examiner* — Jennifer A Berrios
(74) *Attorney, Agent, or Firm* — McNees Wallace & Nurick LLC

(57) ABSTRACT

A water-releasing cosmetic composition in the form of an emulsion and process for preparing the cosmetic composition are provided. The cosmetic composition includes an aqueous phase and an oil phase. The aqueous phase includes a hydrating agent at a concentration, by weight, of about 1% to about 50%. The oil phase includes a silicone polymer, an emulsifying crosslinked siloxane elastomer gel including an emulsifying crosslinked siloxane elastomer, and a hydrophobic silica. The emulsifying crosslinked siloxane elastomer gel includes an emulsifying crosslinked siloxane elastomer at a concentration, by weight of about 0.5% to about 7% based upon weight of the composition. The hydrophobic silica is at a concentration, by weight, of about 0.1% to about 5%, based upon weight of the composition. The cosmetic composition converts from an emulsion to a plurality of droplets upon rubbing.

19 Claims, No Drawings

WATER-RELEASING COSMETIC COMPOSITION INCLUDING A HYDROPHOBIC SILICA

CROSS-REFERENCE TO RELATED APPLICATIONS

This patent application claims the benefit of and is a continuation-in-part of U.S. Non-Provisional patent application Ser. No. 13/529,113 filed on Jun. 21, 2012, and entitled "WATER-RELEASING COSMETIC COMPOSITION INCLUDING A HYDROPHOBIC SILICA AND A CO-EMULSIFIER," the disclosure of which is incorporated by reference as if fully rewritten herein.

FIELD OF THE INVENTION

The present invention is directed to cosmetic compositions and methods of using and producing cosmetic compositions. More specifically, the present invention is directed to a water-releasing cosmetic composition in the form of an emulsion having an aqueous phase including a hydrating agent and an oil phase including a silicone polymer, an emulsifying crosslinked siloxane elastomer gel including an emulsifying crosslinked siloxane elastomer, a hydrophobic silica, and a co-emulsifier. The water-releasing cosmetic composition converts from an emulsion to a plurality of droplets upon rubbing.

BACKGROUND OF THE INVENTION

For various reasons associated in particular with greater comfort of use (softness, emollience and the like), current cosmetic compositions are usually in the form of an emulsion of the oil-in-water (O/W) type consisting of an aqueous-dispersing-continuous phase and an oily-dispersed-discontinuous phase, or of an emulsion of the water-in-oil (W/O) type consisting of an oily-dispersing-continuous phase and an aqueous-dispersed-discontinuous phase. O/W emulsions are usually preferred in the cosmetics field, because O/W emulsions comprise an aqueous phase as external phase, which gives the emulsions, when applied to the skin, a fresher, less greasy, less tacky, and lighter feel than W/O emulsions.

Many compositions, especially cosmetic compositions, have been developed for easy and comfortable application onto a targeted substrate. Unfortunately, many of these compositions are in fact difficult to apply and do not possess a smooth feel upon application. Moreover, compositions often have a tendency to feel tacky, yielding poor application and spreadability characteristics.

Although glycerin is a fairly low cost humectant, problems arise when incorporating high levels of glycerin in cosmetic compositions. Incorporating high levels of glycerin, generally greater than 5%, results in a cosmetic compositions having a tacky and sticky feel upon application to skin. The tacky and sticky feel is undesirable to consumers. Several approaches, such as using light emollients, powders, or combinations thereof may reduce tackiness; however, the resulting cosmetic compositions may not provide sufficient consumer appeal and may still have residual tackiness that can be felt on the skin after application.

Therefore, it is desirable to provide a composition possessing a high level of glycerin without having a tacky feel and that is pleasing to consumers.

A cosmetic composition and methods of using and producing cosmetic compositions that do not suffer from one or more of the above drawbacks would be desirable in the art.

BRIEF DESCRIPTION OF THE INVENTION

In an exemplary embodiment, a water-releasing cosmetic composition in the form of an emulsion is provided. The cosmetic composition includes an aqueous phase and an oil phase. The aqueous phase includes a hydrating agent. The hydrating agent is at a concentration, by weight, of about 1% to about 50%, based upon weight of the composition. The oil phase includes a silicone polymer, an emulsifying crosslinked siloxane elastomer gel including an emulsifying crosslinked siloxane elastomer, and a hydrophobic silica. The emulsifying crosslinked siloxane elastomer gel at a concentration, by weight, of about 3% to about 20%, the emulsifying crosslinked siloxane elastomer gel including a emulsifying crosslinked siloxane elastomer at a concentration, by weight of about 0.5% to about 7% based upon weight of the composition. The hydrophobic silica is at a concentration, by weight, of about 0.1% to about 5%, based upon weight of the composition. The water-releasing cosmetic composition converts from an emulsion to a plurality of droplets upon rubbing.

In another exemplary embodiment, a method for preparing the cosmetic composition is provided. The method includes mixing the aqueous phase at ambient or elevated temperature. The method includes mixing the oil phase at ambient temperature or elevated temperature. The method includes slowly adding the mixed aqueous phase to the mixed oil phase while mixing, forming a water-in-oil emulsion at ambient or elevated temperature.

The present disclosure is also directed to a method for cosmetic treatment of keratinous tissues by applying the above-disclosed water-releasing composition onto a surface of the keratinous tissue.

Other features and advantages of the present invention will be apparent from the following more detailed description of the preferred embodiment which illustrates, by way of example, the principles of the invention.

DETAILED DESCRIPTION OF THE INVENTION

"Keratinous tissue," as used herein, includes but is not limited to skin, hair, and nails.

"Homogenous" means substantially uniform throughout, i.e., a single phase mixture.

In the present application the term "ambient temperature" means a temperature of 25° C.

In the present application the term "water-releasing," as used herein, describes the phenomenon wherein, upon application of a cosmetic composition, the shearing forces generated by the rubbing in or application of the cosmetic composition cause the water-in-oil type emulsion to rupture, thereby causing the internal aqueous phase to emerge in the form of droplets.

The cosmetic compositions and methods of the present invention can comprise, consist of, or consist essentially of the essential elements and limitations of the invention described herein, as well as any additional or optional ingredients, components, or limitations described herein or otherwise useful in personal care compositions intended for topical application to keratinous tissue.

It has been surprisingly discovered by the inventor that high levels of hydrating agents, such as glycerin can be formed into a water-in-oil type emulsion in the form of a gel-like cream that has a transformative water-releasing effect upon rubbing into keratinous tissue. The transformative water-releasing effect is that the cream transforms into droplets containing the aqueous phase upon rubbing the cream into keratinous tissue. It has also been surprisingly discovered by the inventor that the gel-like cream provides a unique and refreshing sensory experience without the tackiness associated with incorporating high levels of hydrating agents like glycerin into cosmetic compositions.

One advantage of an embodiment of the present disclosure includes providing a cosmetic composition for incorporating relatively high levels of hydrating agents or aqueous based moisturizing ingredients (e.g. glycerin). Another advantage of an embodiment of the present disclosure includes providing cosmetic compositions that provide improved skin-feel properties. Yet another advantage of an embodiment of the present disclosure is providing a keratinous tissue treatment composition that has stability against phase separation even under freeze/thaw cycling. Another advantage of an embodiment of the present disclosure includes a keratinous tissue treatment composition that achieves a smooth non-draggy rub-in upon initial application to the keratinous tissue.

The water-in-oil emulsion system of the present water-releasing cosmetic composition has a white, gel-like cream appearance, or it may change to a transparent gel-like or matte appearance by a method of adjusting the refractive index, as known by those in the art. When the cosmetic composition is applied to the skin in a conventional way, the cosmetic composition quickly releases bead-like droplets containing the aqueous phase, bringing about a novel and soothing feeling to consumers.

Aqueous Phase

The aqueous phase present in the cosmetic composition includes glycerin, water, and other aqueous phase ingredients. The aqueous phase of the water-releasing cosmetic composition is at a concentration, by weight, of about 20% to about 85%, or alternatively about 25% to about 80%, or alternatively about 30% to about 75% based upon weight of the cosmetic composition.

Hydrating Agent

The aqueous phase present in the cosmetic composition according to the disclosure includes a hydrating agent at a concentration, by weight, of about 1% to about 50%, or alternatively about 5% to about 40%, or alternatively about 10% to about 30% based upon weight of the composition.

Suitable examples of the hydrating agent, include polyols for example, glycerol, glycols such as butylene glycol, propylene glycol, isoprene glycol, dipropylene glycol, hexylene glycol and polyethylene glycols, sorbitol, sugars such as glucose, and mixtures thereof. According to one preferred embodiment of the invention, the polyol chosen is glycerol, dipropylene glycol or mixtures thereof, or a mixture of glycerol and/or of dipropylene glycol and of one or more other polyols especially chosen from those indicated above: butylene glycol, propylene glycol, isoprene glycol, hexylene glycol, polyethylene glycols, sorbitol, sugars, methylpropanediol and 1,3-propanediol and mixtures thereof. A particularly suitable polyol for use with the present invention is glycerin.

In one embodiment, glycerin is incorporated in the cosmetic composition at levels greater than 5% or alternatively, greater than 10%, by weight, of the cosmetic composition.

Water

The aqueous phase present in the cosmetic composition according to the disclosure includes water at a concentration, by weight, of about 30% to about 85%, or alternatively about 35% to about 80% or alternatively about 40% to about 70%, based upon weight of the composition. The water used may be sterile demineralized water and/or a floral water such as rose water, cornflower water, camomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

Preservative System

The aqueous phase present in the cosmetic composition according to the disclosure includes a preservative system at a concentration, by weight of about 0.1% to about 3%, or alternatively about 0.5% to about 2.5% or alternatively about 1% to about 2.0%, based upon weight of the composition. In a preferred embodiment, the preservative system includes preservative system comprises organic acids, parabens, formaldehyde donors, phenol derivatives, quaternary ammoniums, alcohols, isothiazolones, and combinations thereof.

Examples of organic acid preservative systems include, but are not limited to, sodium benzoate, potassium sorbate, benzoic acid and dehydroaceticic acid, sorbic acid, and combinations thereof. A preferred organic acid preservative system includes a mixture of sodium benzoate and potassium sorbate.

Examples of paraben preservative systems include, but are not limited to, alkyl para-hydroxybenzoates, wherein the alkyl radical has from 1, 2, 3, 4, 5 or 6 carbon atoms and preferably from 1 to 4 carbon atoms e.g., methyl para-hydroxybenzoate (methylparaben), ethyl para-hydroxybenzoate (ethylparaben), propyl para-hydroxybenzoate (propylparaben), butyl para-hydroxybenzoate (butylparaben) and isobutyl para-hydroxybenzoate (isobutylparaben).

Examples of formaldehyde donor preservative systems include, but are not limited to, 1,3-Dimethylol-5,5-dimethylhydantoin (DMDM hydantoin), imidazolidinyl urea, gluteraldehyde, and combinations thereof.

Examples of quaternary ammonium preservative systems include, but are not limited to, benzalkonium chlroide, methene ammonium chloride, benzethonium chloride, and combinations thereof.

Examples of alcohol preservative systems include, but are not limited to, ethanol, benzyl alcohol, dichlorbenzyl alcohol, phenoxyethanol, and combinations thereof.

Examples of isothiazolone preservative systems include, but are not limited to, methylchloroisothiazolinone, methylisothiazolinone, and combinations thereof.

Other suitable preservatives for preservative system include, but are not limited to, chloracetamide, triclosan and iodopropynyl butylcarbamate, pyridine derivatives (e.g., pyrithione and zinc pyrithione), chlorphenesin, phenyl mercuric salts, phenoxyethanol, and other know preservative systems.

Oil Phase

The oil phase present in the cosmetic composition according to the disclosure includes a silicone polymer, an emulsifying crosslinked siloxane elastomer gel including an emulsifying siloxane elastomer, a hydrophobic silica, and, optionally, a co-emulsifier.

Silicone Polymer

The oil phase present in the cosmetic composition according to the disclosure includes silicone polymer is at a concentration, by weight of about 1% to about 40%, or alternatively about 5% to about 35%, or alternatively about 10% to about 30%, based upon weight of the composition. Suitable example of silicone polymers include, but are not limited to, polydimethylsiloxane (dimethicone), a mixture of dimethicone and dimethiconol, decamethylcyclopentasiloxane (D5), cyclomethicone (mixture of D4, D5 and D6), and combinations thereof.

Emulsifying Crosslinked Siloxane Elastomer Gel

The oil phase present in the cosmetic composition according to the disclosure includes an emulsifying crosslinked siloxane elastomer gel at a concentration, by weight, of about 3% to about 20%, or alternatively about 4% to about 15%, or alternatively about 5% to about 10%, based upon weight of the composition. The emulsifying crosslinked siloxane elastomer gel includes an emulsifying crosslinked siloxane elastomer and a swelling solvent. Examples of suitable emulsifying crosslinked siloxane elastomer gels, include, but are not limited to, substituted or unsubstituted dimethicone/copolyol crosspolymer, dimethicone and dimethicone/PEG-10/15 crosspolymers, substituted or unsubstituted dimethicone/polyglyceral crosspolymer, dimethicone and dimethicone/polyglycerin-3 crosspolymer. Such suitable emulsifying crosslinked siloxane elastomer gels are sold or made, for example, under the names of "KSG-210" a polyether-modified cross polymer with an INCI name of dimethicone (and) dimeticon/PEG-10/15 crosspolymer, and "KSG-710" a polyglycerin-modified crosspolymer with and INCI name of dimethicone (and) dimethicone/polyglycerin-3 crosspolymer, both available from ShinEtsu Silicones of America, Inc. (Akron, Ohio). The emulsifying crosslinked siloxane elastomer gel includes an emulsifying crosslinked siloxane elastomer in an amount of about 0.5% to about 7.0% or alternatively about 0.8% to about 3.0%, or alternatively about 1.0% to about 2.0%, or alternatively about 1.2%, based upon weight of the composition.

Hydrophobic Silica

The oil phase present in the cosmetic composition according to the disclosure includes a hydrophobic silica at a concentration, by weight, of about 0.1% to about 5%, or alternatively about 0.1% to about 2% or alternatively about 0.1% to about 1%, based upon weight of the composition. If the hydrophobic silica concentration exceeds 5% by weight of the cosmetic composition, then the cosmetic composition becomes gritty, which is undesirable to users.

As used herein, hydrophobic silica includes hydrophobic fumed silica, hydrophobic precipitation-process silica, hydrophobic aerogels of silica. After substitution with alkyl groups, hydrophobic silica products are classified according to the different substitution groups into silylated silica, dimethyl-silylated silica, trimethyl-silylated silica and polydimethylsiloxane-silylated silica.

Suitable examples of hydrophobic fumed silica, include, but are not limited to the commercial products AEROSIL® 8202, AEROSIL® R972, AEROSIL® R805, AEROSIL® R8200, AEROSIL® R974, AEROSIL® R812S and AEROSIL® R812 available from Evonik Degussa GmbH through the subsidiary North America Evonik Degussa Corporation (Piscataway, N.J.).

According to an embodiment of the invention, hydrophobic silica is a hydrophobic aerogel of silica.

As used here, "silica aerogels" are porous materials obtained by replacing (by drying) the liquid component of a silica gel with air. Silica aerogels are generally synthesized via a sol-gel process in a liquid medium and then dried, usually by extraction with a supercritical fluid, such as, but not limited to supercritical carbon dioxide ($CO_2$). This type of drying makes it possible to avoid shrinkage of the pores and of the material. The sol-gel process and the various drying processes are described in detail in Brinker C J., and Scherer G. W., Sol-Gel Science: New York: Academic Press, 1990.

The hydrophobic silica aerogel particles used in the present invention have a specific surface area per unit of mass ($S_M$) ranging from about 500 to about 1500 m$^2$/g, or alternatively from about 600 to about 1200 m$^2$/g, or alternatively from about 600 to about 800 m$^2$/g, and a size expressed as the mean volume diameter (D[0.5]), ranging from about 1 to about 30 μm, or alternatively from about 5 to about 25 μm, or alternatively from about 5 to about 20 μm, or alternatively from about 5 to about 15 μm. The specific surface area per unit of mass may be determined via the BET (Brunauer-Emmett-Teller) nitrogen absorption method described in the *Journal of the American Chemical Society*, vol. 60, page 309, February 1938, corresponding to the international standard ISO 5794/1. The BET specific surface area corresponds to the total specific surface area of the particles under consideration.

The size of the silica aerogel particles may be measured by static light scattering using a commercial granulometer such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is especially described in the publication by Van de Hulst, H. C., "Light Scattering by Small Particles," Chapters 9 and 10, Wiley, New York, 1957.

The silica aerogel particles used in the present invention may advantageously have a tamped (or tapped) density) ranging from about 0.04 g/cm$^3$ to about 0.10 g/cm$^3$' or alternatively from about 0.05 g/cm$^3$ to about 0.08 g/cm$^3$. In the context of the present invention, this density, known as the tamped density, may be assessed according to the following protocol: 40 g of powder are poured into a measuring cylinder; the measuring cylinder is then placed on a Stav 2003 machine from Stampf Volumeter; the measuring cylinder is then subjected to a series of 2500 packing motions (this operation is repeated until the difference in volume between two consecutive tests is less than 2%); the final volume Vf of packed powder is then measured directly on the measuring cylinder. The tamped density is determined by the ratio m/Vf, in this instance 40/Vf (Vf being expressed in cm$^3$ and m in g).

According to one embodiment, the hydrophobic silica aerogel particles used in the present invention have a specific surface area per unit of volume $S_V$ ranging from about 5 to about 60 m$^2$/cm$^3$, or alternatively from about 10 to about 50 m$^2$/cm$^3$, or alternatively from about 15 to about 40 m$^2$/cm$^3$. The specific surface area per unit of volume is given by the relationship: $S_V=S_M r$ where r is the tamped density expressed in g/cm$^3$ and $S_M$ is the specific surface area per unit of mass expressed in m$^2$/g, as defined above.

Preferably, the hydrophobic silica aerogel particles according to the invention have an oil-absorbing capacity, measured at the wet point, ranging from about 5 to about 18 ml/g, or alternatively from about 6 to about 15 ml/g, or alternatively from about 8 to about 12 ml/g. The oil-absorbing capacity measured at the wet point, noted Wp, corresponds to the amount of water that needs to be added to 100 g of particle in order to obtain a homogeneous paste. Wp is measured according to the wet point method or the method for determining the oil uptake of a powder described in standard NF T 30-022. Wp corresponds to the amount of oil adsorbed onto the available surface of the powder and/or absorbed by the powder by measuring the wet point, described below: An amount=2 g of powder is placed on a glass plate, and the oil (isononyl isononanoate) is then added dropwise. After addition of 4 to 5 drops of oil to the powder, mixing is performed using a spatula, and addition of oil is continued until a conglomerate of oil and powder has formed. At this point, the oil is added one drop at a time and the mixture is then triturated with the spatula. The addition of oil is stopped when a firm, smooth paste is obtained. This paste must be able to be spread on the glass plate without cracking or forming lumps. The volume Vs (expressed in ml) of oil used is then noted. The oil uptake corresponds to the ratio Vs/m.

The aerogels used according to the present invention are hydrophobic silica aerogels, preferably of silylated silica (INCI name: silica silylate). The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups. Preparation of hydrophobic silica aerogels particles that have been surface-modified by silylation, is found in U.S. Pat. No. 7,470,725, incorporated herein by reference. In one embodiment, hydrophobic silica aerogels particles surface-modified with trimethylsilyl groups are preferred.

Suitable examples of hydrophobic silica aerogels, includes, but are not limited to, the aerogels sold under the trade names of VM-2260 (INCI name: Silica silylate), VM-2270 (INCI name: Silica silylate), both available from Dow Corning Corporation (Midland, Mich.). The particles of VM-2260 have a mean size of about 1000 microns and a specific surface area per unit of mass ranging from 600 to 800 $m^2/g$. The particles of VM-2270 have a mean size ranging from 5-15 microns and a specific surface area per unit of mass ranging from 600 to 800 $m^2/g$. Another suitable example of a hydrophobic silica aerogel includes, but is not limited to, the aerogels commercial available from Cabot Corporation (Billerica, Mass.) under the trade name of Aerogel TLD 201, Aerogel OGD 201 and Aerogel TLD 203, Enova Aerogel MT 1100 and Enova Aerogel MT 1200.

Co-Emulsifier

The oil phase present in the cosmetic composition according to the disclosure optionally includes a co-emulsifier at a concentration, by weight, of about 0.01% to about 1%, or alternatively about 0.05% to about 0.9%, or alternatively about 0.07% to about 0.5%, or alternatively about 0.1% to about 0.8%, or alternatively about 0.1% to about 0.5%, or alternatively about 0.1%, based upon weight of the composition. If the co-emulsifier concentration exceeds 1% by weight of the cosmetic composition, then the cosmetic composition may still form an emulsion but the desirable transformative effect of cream changing to droplets upon rubbing is lost.

Suitable examples of co-emulsifiers include polyether substituted linear or branched polysiloxane copolymers. One preferred co-emulsifier is PEG-10 dimethicone available under the tradename of ES-5612 from Dow Corning Corporation (Midland, Mich.), or KF-6017 from Shin-Etsu (Akron, Ohio). Another preferred co-emulsifier is dimethicone (and) PEG/PPG-18/18 dimethicone available under the tradename of ES-5226 DM from Dow Corning Corporation (Midland, Mich.) Other suitable co-emulsifiers include, PEG-9 polydimethylsiloxyethyl dimethicone available under the tradename KF-6028 and PEG-9, lauryl PEG-9 polydimethylsiloxyethyl dimethicone available under the tradename KF-6038, both available from Shin-Etsu (Akron, Ohio).

Active Ingredient

The aqueous phase or the oil phase, depending on the nature of the active ingredient, includes an active ingredient. The cosmetic composition according to the disclosure includes an active ingredient at a concentration, by weight, of about 0.01% to about 5%, or alternatively about 0.05% to about 4%, or alternatively about 0.1% to about 3%, based upon weight of the composition. In one embodiment, the active ingredient is capryloyl salicylic acid, adenosine, baicalin, resveratrol, other polyphenols, or combinations thereof. In another embodiment, the active ingredient is an organic or inorganic UV filter, or combination thereof.

Fragrance

Fragrance including natural or synthetic odoriferous substances or mixtures thereof may be included in the cosmetic composition of the present disclosure. Use may be made of mixtures of different odoriferous substances which together generate an attractive scent. Natural odoriferous substances are extracts of flowers (lily, lavender, rose, jasmine, neroli or ylang-ylang), stems and leaves (geranium, patchouli, petitgrain), fruits (anis, coriander, caraway, juniper), fruit rinds (bergamot, lemon, orange), roots (mace, angelica, celery, cardamom, costus, iris, thyme), needles and twigs (spruce, fir, pine, mountain pine) and resins and balsams (galbanum, elemi, benzoin, myrrh, frankincense, opoponax). Typical synthetic perfume compounds are products of the esters, ethers, aldehydes, ketones, alcohols and hydrocarbon types. Essential oils of low volatility, which are generally used as flavoring components, are also suitable as fragrances, for example, but not limited to, sage oil, camomile oil, clove oil, balm oil, peppermint oil, cinnamon leaf oil, linden blossom oil, juniper berry oil, vetiver oil, frankincense oil, galbanum oil, labdanum oil and lavandin oil.

Optional Powders

The composition of the present disclosure may optionally include cosmetic powders. The optional cosmetic powders provide formulas that are smoother and softer on the skin. Representative cosmetic powders include, but are not limited to talc, mica, magnesium carbonate, calcium carbonate, magnesium silicate, aluminum magnesium silicate, silica, titanium dioxide, zinc oxide, red iron oxide, yellow iron oxide, black iron oxide, polyethylene powder, methacrylate powder, polystyrene powder, silk powder, crystalline cellulose, starch, titanated mica, iron oxide titanated mica, bismuth oxychloride, and the like. Additional powders include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide. A representative cosmetic powder includes, for example, polymethylsilsesquioxane. Cosmetic powders may be present in the compositions in amounts generally ranging from about 0.1% to about 10% by weight of the composition.

The composition of the present disclosure may also contain cosmetically acceptable additives or adjuvants as well as cosmetic or dermatologic active agents. Representative additives and adjuvants include, for example, water-soluble or water-miscible solvents or co-solvents, dispersion enhancing agents, moisturizers, colorants, fillers, antioxidants (e.g., EDTA, BHT, tocopherol), essential oils, fragrances, dyes, neutralizing or pH-adjusting agents (e.g., citric acid, triethylamine (TEA) and sodium hydroxide), conditioning or softening agents (e.g., panthenol and allantoinin) and extracts such as botanical extracts. Additives and adjuvants may be present in the compositions in amounts generally ranging from about 0.01% to about 10% by weight. Examples of cosmetic active agents or dermatological active agents include sunscreen agents (e.g., inorganic sunscreen agent, such as titanium dioxide and zinc oxide and organic sunscreen agents, such as octocrylene, ethylhexyl methoxycinnamate, and avobenzone), free-radical scavengers, keratolytic agents, vitamins (e.g., Vitamin E and derivatives thereof), anti-elastase and anti-collagenase agents, peptides, fatty acid derivatives, steroids, trace elements, extracts of algae and of planktons, enzymes and coenzymes, flavonoids and ceramides, hydroxy acids and mixtures thereof, and enhancing agents. These ingredients may be soluble or dispersible in whatever phase or phases is/are present in the cosmetic composition (i.e., aqueous and/or fatty (oil) phase).

Hydration Index

The cosmetic composition of the present disclosure has a hydration index of about 1.34 or higher.

The hydration index is calculated using the following equation $$IP_{1h} = \frac{\text{Average}[(T_{1h} - T_0)_{formula} - (T_{1h} - T_0)_{bare\ skin}]}{\text{Average}[(T_{1h} - T_0)_{reference} - (T_{1h} - T_0)_{bare\ skin}]}$$

where $IP_{1h}$ is the hydration index of the skin; $T_{1h}$ is the Corneometer reading one hour after applying the formula or reference, $T_0$ is the initial Corneometer reading right after applying the formula or reference, $(T_{1h}-T_0)_{formula}$ is the difference between the Corneometer reading one hour after applying the formula of the present disclosure to the skin and the Corneometer reading right after applying the formula of the present disclosure to the skin; $(T_{1h}-T_0)_{bare\ skin}$ is the difference between the Corneometer reading at the one hour mark and initial reading of bare skin; $(T_{in}-T_0)_{refererence}$ is the difference between the Corneometer reading one hour after applying the reference cream (containing 7% glycerin) to the skin and Corneometer reading right after applying the reference cream (containing 7% glycerin) to the skin. The Corneometer readings were taken at ambient temperatures.

The Corneometer used to measure the hydration index was Corneometer™ CM825, available from Courage+Khazaka, Köln, Germany.

Process

The method for preparing the water-releasing cosmetic composition of the present disclosure, according to one embodiment, includes creating a stable water-in-oil emulsion with or without heating. In one embodiment, the process uses a cold-processing method which keeps the temperature below 30° C. and more preferably at ambient temperature during emulsification. In an alternative embodiment, the process includes heating the water and oil phases to an elevated temperature which includes temperatures above 30° C. to form the emulsion. The process includes mixing a first phase (aqueous) including glycerin, water, and other ingredients. In one embodiment, the pH of the aqueous phase is adjusted using suitable and well-known pH adjusters to prevent mold formation. The process includes mixing a second phase (oil) including a silicone polymer, an emulsifying crosslinked siloxane elastomer gel, and, a co-emulsifier. The process includes very slowly adding the first phase (aqueous) to the second phase (oil) while mixing and as viscosity of the mixture increase, mixing speed is increased to about 1200 rpm. After the first phase (aqueous) is mixed into the second phase (oil) a white, trembling gel-like cream is formed. To the gel-like cream the preservative system is added along with other ingredients, such as but not limited to, fragrance, and active ingredients (e.g. capryloyl salicylic acid). Mixing paddle is changed to a U-shaped paddle and a hydrophobic silica is added (e.g., silica silylate). The cosmetic composition is in the form of a white gel-like cream that provides a water-releasing effect by releasing droplets upon rubbing the gel-like cream into keratinous tissue.

Viscosity

Viscosity is measured using Brookfield Viscometer, in centipoise (mPa·s) using spindle T-D with speed set at 10 rpm. In one embodiment, the viscosity of the cosmetic composition is about 35,000 to 55,000 cp (mPa·s).

Water-Releasing Effect

With respect to the present invention, a good water-releasing effect of the water-in-oil emulsion means that the water-releasing effect has an evaluation result of more than or equal to a score of 3 in the evaluation system described below. The test method and evaluation score of the test system are described below.

About 0.2 g of a water-in-oil emulsion sample of cosmetic composition is taken and placed on the back of a hand, then it is applied thereon by circling gently with the middle finger and ring finger of the other hand, and then the phenomenon of the water-releasing effect is observed when the circling application reaches 20 cycles, and evaluated by a 5-level scoring system. A score of 5 represents that more than 10 bead-like water drops having an average diameter of more than or equal to 3 mm appear, or more than 20 bead-like water drops having an average diameter of more than or equal to 1 mm appear. A score of 4 represents that 2-10 bead-like water drops having an average diameter of more than or equal to 3 mm appear, or 10-20 bead-like water drops having an average diameter of more than or equal to 1 mm appear and the bead-like water drops having an average of more than or equal to 3 mm are no more than 10. A score of 3 represents that 2-9 bead-like water drops having an average diameter of more than or equal to 1 mm appear and there is at most 1 bead-like water drop having an average diameter of more than or equal to 3 mm, or 10-20 bead-like water drops having an average diameter of 1 mm appear. A score of 2 represents that 2-9 bead-like water drops having an average diameter of 1 mm appear. A score of 1 represents that no water drop appears. Each level between scores 5 to 4, 4 to 3, 3 to 2, and 2 to 1 shows that the water-releasing effect is between the two end values described above, and the lower the score, the poorer the water-releasing effect.

In one embodiment, the water-releasing effect of the cosmetic composition of the present disclosure is about 4 to 5. In embodiments, having higher levels of glycerin, namely greater than 30%, the water-releasing effect of the cosmetic composition of the present disclosure is about 2 to 3.

The water-silicone boundary of the water-in-oil emulsion of the present disclosure is stable. The water-in-oil emulsion of the present disclosure includes an external or oil (silicone) phase surrounding non-uniform and larger droplet sizes of the internal aqueous phase. The non-uniform aqueous droplets range in size from approximately 0.1 microns to about 50 microns in diameter, with some aqueous drops having a diameter of about 10 to 20 microns.

Tackiness Test

The tackiness of the cosmetic compositions is measured using a TA.XT Plus Texture Analyzer. The cosmetic composition is evenly applied on a Leneta drawdown card in the amount of 0.1 g over an area of 2 cm×6.5 cm and allowed to air-dry for 2 min. The drawdown card with cosmetic composition or test product is mounted on a testing platform. The measurement is made using a tack probe and is recorded with Exponent 32 software. The average of six (6) measurements for each formula is used in the analysis. The tackiness of the test product is expressed as the force (in Newtons) required to lift the tack probe from the test product surface. The higher the force required to remove the tack probe from the test product surface, the tackier the cosmetic composition. Generally, tackiness levels of greater than about 20 Newtons will register a "tackiness" feeling with consumers. Tackiness levels of less than 20 Newtons are generally not considered to be "tacky" by consumers.

Upon application of the water-releasing cosmetic composition to keratinous tissue, the aqueous phase droplets are released from the emulsion and form droplets on the surface of a keratinous tissue as a result of the shearing forces used to apply the cosmetic composition to the keratinous tissue.

A method for treating keratinous tissue includes applying to the keratinous tissue the cosmetic composition of the present disclosure. The cosmetic composition of the present disclosure is in any desirable cosmetic form, such as, but not limited to, liquid lotions, creams, and mousses, can be applied to keratinous tissue to provide greater hydration.

The following examples are intended to further illustrate the present invention. They are not intended to limit the invention in any way. Unless otherwise indicated, all parts are by weight.

EXAMPLES

TABLE 1

| Phase | INCI Name | Example 1 (inventive) | Example 2 (inventive) | Example 3 (comparative) | Example 4 (comparative) |
|---|---|---|---|---|---|
| A | DIMETHICONE (and) DIMETHICONE/PEG-10/15 CROSSPOLYMER* | 5 | 5 | 5 | 5 |
| A | PEG-10 DIMETHICONE | 0.1 | 0.1 | 0.1 | 0.1 |
| A | DIMETHICONE (and) DIMETHICONOL | 1 | 1 | 1 | 1 |
| A | DIMETHICONE | 10 | 10 | 10 | 10 |
| B | Water | QS | QS | QS | QS |
| B | Glycerin | 15 | 45 | 15 | 0 |
| B | PHENOXYETHANOL | 0.5 | 0.5 | 0.5 | 0.5 |
| B | DISODIUM EDTA | 0.1 | 0.1 | 0.1 | 0.1 |
| B | Sodium Citrate | 0.2 | 0.2 | 0.2 | 0.2 |
| B | Sodium Chloride | 0.8 | 0.8 | 0.8 | 0.8 |
| C | Alcohol Denat. | 3 | 3 | 3 | 3 |
| C | Propanediol | 5 | 5 | 5 | 5 |
| C | p-ANISIC ACID | 0.15 | 0.15 | 0.15 | 0.15 |
| C | CAPRYLOYL SALICYLIC ACID | 0.1 | 0.1 | 0.1 | 0.1 |
| C | FRAGRANCE | 0.25 | 0.25 | 0.25 | 0.25 |
| D | SILICA SILYLATE | 0.5 | 0.5 | 0 | 0.5 |
| | Total (%): | 100 | 100 | 100 | 100 |
| | Amount of emulsifying crosslinked siloxand elastomer (wt % of total composition) | 1.2 | 1.2 | 1.2 | 1.2 |
| | Texture | White, trembling gel-like cream. Water droplets released upon rubbing. | White, translucent gel-like cream. Small water droplets released upon rubbing. | White lotion. Some noticeable water droplets released upon rubbing. | White cream. Water droplets released upon rubbing. |
| | Microscope | W/Si, boundary ok, large water droplet size. | W/Si, boundary ok, water droplets are smaller and more uniform than Example 1 | W/Si, boundary ok, large water droplet size | W/Si, boundary ok, large water droplet |
| | Viscosity (cp) | 53,000 | 37,000 | 10,000 | 60,000 |
| | Tackiness (Newtons) | 13.06 | 10.19N | 21.92 | 8.99N |
| | Water-Releasing Effect | 4 to 5 | 2 to 3 | 3 | 4 to 5 |

*emulsifying crosslinked siloxane elastomer gel

TABLE 2

| Phase | INCI Name | Example 5 (comparative) |
|---|---|---|
| A | POLYGLYCERYL-4 DIISOSTEARATE/ POLYHYDROXYSTEARATE/SEBACATE | 3 |
| A | ETHYLHEXYL PALMITATE | 7 |
| A | CAPRYLIC/CAPRIC TRIGLYCERIDE | 4 |
| A | OCTYLDODECANOL | 4 |
| A | PENTAERYTHRITYL TETRAETHYLHEXANOATE | 1 |
| B | WATER | QS |
| B | GLYCERIN | 10 |
| B | SODIUM CHLORIDE | 2 |
| B | Preservatives | QS |
| | Total (%): | 100 |
| | Texture | Glossy white lotion |
| | Microscope | W/O with very fine water droplets |
| | Viscosity (cp) | 14,200 |
| | Tackiness (Newtons) | 29.63 |
| | Water-Releasing Effect | 1 |

The method of making each of the examples provided in Tables 1 and 2 is generally the same. The examples in Table 1 include inventive examples and comparative examples having a water-releasing effect. The example in Table 2 is a comparative of a well-known water-in-oil emulsion that illustrates the tackiness of glycerin and does not have a water-releasing effect.

In making each of the examples in Tables 1 and 2, the following procedure is used. The ingredients of Phase B (aqueous) are mixed together in a side kettle at ambient temperature or higher. The ingredients of Phase A (oil phase) are mixed together in a main kettle at ambient temperature or higher. The mixture of Phase B ingredients (aqueous phase) is slowly added to the mixture of Phase A ingredients (oil phase), usually drop wise, while mixing. As viscosity of the mixture increases, mixing speed in the main kettle is increased to about 1200 rpm. After the first phase (aqueous) is mixed into the second phase (oil) a water-in-oil emulsion is formed. In the Examples of Table 1, Phase C (preservative system and/or other ingredients) is added to the water-in-oil emulsion. For the Examples of Table 1, the mixing paddle is changed to a U-shaped paddle and Phase D (a hydrophobic silica) is added.

Example 1

The water-in-oil emulsion of inventive Example 1 is prepared according to the procedure outlined above. Example 1 includes 15% glycerin. The emulsion formed in Example 1 is a white, trembling gel-like cream that releases droplets upon rubbing. The water/silicone emulsion boundary layer is stable and includes droplets having various droplet sizes, with some droplets as large as 50 microns or greater. The viscosity of Example 1 is measured using a Brookfield Viscometer, using spindle T-D and speed set at 10 rpm. The viscosity of Example 1 is about 53,000 cp (mPa·s). The tackiness of Example 1 is measured using a TA.XT Plus Texture Analyzer. The tackiness of Example 1 is 13.06 Newtons, which indicates little or no tackiness feeling when applied to the skin. The water-releasing effect of Example 1 is measured by placing about 0.2 g of the cosmetic composition on the back of a hand, then applying thereon by circling gently with the middle finger and ring finger of the other hand. The phenomenon of the water-releasing effect is observed when the circling application reaches 20 cycles. Approximately 7-8 bead-like droplets of more than or equal to 3 mm appears and approximately 17-19 bead-like droplets having an average diameter of more than or equal to 1 mm appear. The water-releasing effect of the water-in-oil emulsion of Example 1 is about 4 to 5. The hydration index of Example 1 is measured as greater than about 1.34.

Example 2

The water-in-oil emulsion of inventive Example 2 is prepared according to the procedure outlined above. Example 2 includes 45% glycerin. The emulsion formed in Example 2 is a white, translucent gel-like cream that releases small droplets upon rubbing. The water/silicone emulsion boundary layer is stable with various droplet sizes, including some droplets ranging from 10 to 20 microns. The viscosity of Example 2 is measured using a Brookfield Viscometer, using spindle T-D and speed set at 10 rpm. The viscosity of Example 2 is 37,000 cp (mPa·s). The tackiness of Example 2 is measured using a TA.XT Plus Texture Analyzer as described above. The tackiness of Example 2 is 10.19 Newtons, which indicates there is little or no tackiness feeling when applied to the skin. The water-releasing effect of Example 2 is measured by placing about 0.2 g of the cosmetic composition on the back of a hand. The cosmetic composition is then applied thereon by circling gently with the middle finger and ring finger of the other hand. The phenomenon of the water-releasing effect is observed when the circling application reaches about 20 cycles. Approximately 9-11 bead-like droplets having an average diameter of 1 mm appear. The water-releasing effect of the water-in-oil emulsion of Example 2 is about 3 to 4. Example 2 incorporates very high levels of glycerin and does not have a tacky feel.

Example 3

The water-in-oil emulsion of Example 3 is a comparative example and is prepared according to the procedure outlined above. Example 3 includes 15% glycerin but does not include a hydrophobic silica. The emulsion formed in Example 3 is a white lotion that releases droplets upon rubbing. The water/silicone emulsion boundary layer is stable with various droplet sizes, including some droplets as large as 20 to 30 microns. The viscosity of Example 3 is measured using a Brookfield Viscometer, using spindle T-D and speed set at 10 rpm. The viscosity of Example 3 is 10,000 cp (mPa·s). The tackiness of Example 3 is measured using a TA.XT Plus Texture Analyzer. The tackiness of Example 3 is 21.92 Newtons. The tackiness of Example 4 is greater than 20 Newtons, as such, Example 3 feels tackier than Examples 1 and 2, when applied to the skin. The water-releasing effect of Example 3 is measured by placing about 0.2 g of the cosmetic composition on the back of a hand. The cosmetic composition is then applied thereon by circling gently with the middle finger and ring finger of the other hand. The phenomenon of the water-releasing effect is observed when the circling application reaches 20 cycles. Approximately 11-15 bead-like droplets having an average diameter of about 1 mm appear. The water-releasing effect of the water-in-oil emulsion of Example 3 is about 3. Although Example 3 includes glycerin providing a hydrating effect, Example 3 does not include a hydrophobic silica and is tacky and undesirable to consumers.

Example 4

The water-in-oil emulsion of Example 4 is a comparative example and is prepared according to the procedure outlined above. Example 4 does not include glycerin. The emulsion formed in Example 4 is a white cream that releases droplets upon rubbing. The water/silicone emulsion boundary layer is stable with various droplet sizes. The viscosity of Example 4 is measured using a Brookfield Viscometer, using spindle T-D and speed set at 10 rpm. The viscosity of Example 4 is 60,000 cp (mPa·s). The tackiness of Example 4 is measured using a TA.XT Plus Texture Analyzer. The tackiness of Example 4 is 8.99 Newtons. Example 4 has little or no tackiness feeling when applied to the skin. The water-releasing effect of Example 4 is measured by placing about 0.2 g of the cosmetic composition on the back of a hand. The cosmetic composition is then applied thereon by circling gently with the middle finger and ring finger of the other hand. The phenomenon of the water-releasing effect is observed when the circling application reaches 20 cycles. Approximately 5-7 bead-like droplets of more than or equal to 3 mm appear and approximately 15-18 bead-like droplets having an average diameter of more than or equal to 1 mm appear. The water-releasing effect of the water-in-oil emulsion of Example 4 is about 4 to 5. Example 4 does not include glycerin; therefore, Example 4 does not provide the hydrating and moisturizing properties of inventive Examples 1 and 2.

Example 5

The water-in-oil emulsion of Example 5 is a comparative example and is prepared according to the procedure outlined above. The water-in-oil emulsion of Example 5 is a typical water-in-oil emulsion. Example 5 includes about 10% by weight glycerin. The emulsion formed in Example 5 is a glossy white lotion that does not release droplets upon rubbing. The water/oil emulsion boundary layer is stable and includes uniform droplets evenly dispersed within the emulsion. The viscosity of Example 5 is measured using a Brookfield Viscometer, using spindle T-D and speed set at 10 rpm. The viscosity of Example 5 is 14,200 cp (mPa·s). The tackiness of Example 5 is measured using a TA.XT Plus Texture Analyzer for a tackiness of 29.63 Newtons. The tackiness of Example 5 is greater than 20 Newtons, as such, Example 5 feels tacky when applied to the skin. The water-releasing effect of Example 5 is measured by placing about 0.2 g of the cosmetic composition on the back of a hand. The cosmetic composition is applied thereon by circling gently with the middle finger and ring finger of the other hand. The phenomenon of the water-releasing effect is observed when the circling application reaches 20 cycles. No bead-like droplets having an average diameter of more than or equal to 1 mm appeared. The water-releasing effect of the water-in-oil emulsion of Example 5 is about 1; therefore, Example 5 has no water-releasing effect and is tacky, which undesirable to consumers.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A water-releasing cosmetic composition in the form of an emulsion, the composition comprising:
   an aqueous phase including:
      a hydrating agent at a concentration, by weight, of about 1% to about 50%, based upon weight of the composition; and
   an oil phase consisting of:
      a silicone polymer selected from dimethicone, a mixture of dimethicone and dimethiconol, decamethylcyclopentasiloxane, cyclomethicone, and combinations thereof;
      an emulsifying crosslinked siloxane elastomer gel at a concentration, by weight, based upon the weight of the composition, of about 3% to about 20%, the emulsifying crosslinked siloxane elastomer gel comprising an emulsifying crosslinked siloxane elastomer at a concentration, by weight, of about 0.5% to about 7%, based upon weight of the composition;
      a co-emulsifier at a concentration, by weight, of about 0.01% to about 1%, based upon the weight of the composition, wherein the co-emulsifier is selected from polyether substituted linear or branched polysiloxane copolymers; and
      a hydrophobic silica at a concentration, by weight, of about 0.1% to 0.5%, based upon weight of the composition;
   wherein the cosmetic composition converts from an emulsion to a plurality of droplets upon rubbing and has stability against phase separation prior to rubbing.

2. The cosmetic composition of claim 1, wherein the co-emulsifier is at a concentration, by weight of about 0.07% to about 0.5%, based upon weight of the composition.

3. The cosmetic composition of claim 1, wherein the hydrating agent is glycerin.

4. The cosmetic composition of claim 1, wherein the emulsifying crosslinked siloxane elastomer comprises a substituted or unsubstituted dimethicone/copolyol crosspolymer.

5. The cosmetic composition of claim 4, wherein the emulsifying crosslinked siloxane elastomer is dimethicone/PEG-10/15 crosspolymer.

6. The cosmetic composition of claim 1, wherein the emulsifying crosslinked siloxane elastomer comprises a substituted or unsubstituted dimethicone/polyglyceral crosspolymer.

7. The cosmetic composition of claim 6, wherein the emulsifying crosslinked siloxane elastomer is dimethicone/polyglycerin-3 crosspolymer.

8. The cosmetic composition of claim 1, wherein the emulsifying crosslinked siloxane elastomer is at a concentration, by weight, of about 0.7% to about 3.0%, based upon weight of the composition.

9. The cosmetic composition of claim 1, wherein the emulsifying crosslinked siloxane elastomer is at a concentration, by weight, of about 1.0% to about 2.0%, based upon weight of the composition.

10. The cosmetic composition of claim 1, wherein the hydrophobic silica is at a concentration, by weight, of 0.5%, based upon weight of the composition.

11. The cosmetic composition of claim 1, wherein the aqueous phase of the composition further includes an active ingredient.

12. The cosmetic composition of claim 1, wherein the aqueous phase of the composition further includes water, at a concentration, by weight, of about 30% to about 85%, based upon the weight of the composition.

13. The cosmetic composition of claim 1, wherein the silicone polymer is at a concentration, by weight, of about 1% to about 40%, based upon weight of the composition.

14. The cosmetic composition of claim 1, wherein the co-emulsifier is selected from PEG-10 dimethicone, PEG-9 polydimethylsiloxyethyl dimethicone and PEG-9, lauryl PEG-9 polydimethylsiloxyethyl dimethicone, dimethicone and PEG/PPG-18/18 dimethicone, and combinations thereof.

15. The cosmetic composition of claim 1, wherein the composition has a hydration index of about 1.34 or higher.

16. The cosmetic composition of claim 1, wherein the composition further includes cosmetic powder.

17. A water-releasing cosmetic composition in the form of an emulsion, the composition comprising:
- an aqueous phase including:
  - a hydrating agent at a concentration, by weight, of about 5% to about 40%, based upon weight of the composition; and
- an oil phase consisting of:
  - a silicone polymer at a concentration, by weight, of about 5% to about 35%, based upon weight of the composition, the silicone polymer selected from dimethicone, a mixture of dimethicone and dimethiconol, decamethylcyclopentasiloxane, cyclomethicone, and mixtures thereof;
  - an emulsifying crosslinked siloxane elastomer gel at a concentration, by weight, based upon the weight of the composition, of about 3% to about 20%, the emulsifying crosslinked siloxane elastomer gel comprising an emulsifying crosslinked siloxane elastomer at a concentration, by weight, of about 0.8% to about 3%, based upon weight of the composition;
  - a co-emulsifier at a concentration, by weight, of about 0.01% to about 1%, based upon the weight of the composition, wherein the co-emulsifier is selected from polyether substituted linear or branched polysiloxane copolymers; and
  - a hydrophobic silica at a concentration, by weight, of 0.5% based upon weight of the composition;
- wherein the cosmetic composition converts from an emulsion to a plurality of droplets upon rubbing and has stability against phase separation prior to rubbing.

18. A water-releasing cosmetic composition according to claim 17, wherein the concentration of the emulsifying crosslinked siloxane elastomer is about 1.2%, wherein the concentration by weight of the co-emulsifier is about 0.07% to about 0.5%, and wherein the hydrating agent is present at a concentration, by weight, of about 10% to about 30%.

19. A water-releasing cosmetic composition in the form of an emulsion, the composition comprising:
- an aqueous phase including:
  - a hydrating agent at a concentration, by weight, of about 5% to about 40%, based upon weight of the composition; and
- an oil phase consisting of:
  - a silicone polymer at a concentration, by weight, of about 5% to about 35%, based upon weight of the composition, the silicone polymer selected from dimethicone, a mixture of dimethicone and dimethiconol, decamethylcyclopentasiloxane, cyclomethicone, and mixtures thereof;
  - an emulsifying crosslinked siloxane elastomer gel at a concentration, by weight, based upon the weight of the composition, of about 3% to about 20%, the emulsifying crosslinked siloxane elastomer gel comprising an emulsifying crosslinked siloxane elastomer at a concentration, by weight, of about 0.8% to about 3%, based upon weight of the composition; and
  - a hydrophobic silica at a concentration, by weight, of 0.1% based upon weight of the composition;
- wherein the cosmetic composition converts from an emulsion to a plurality of droplets upon rubbing and has stability against phase separation prior to rubbing.

\* \* \* \* \*